United States Patent [19]

McRae

[11] Patent Number: Plant 6,326

[45] Date of Patent: Oct. 11, 1988

[54] LILY PLANT NAMED 'SNOWCAP'

[75] Inventor: Edward A. McRae, Boring, Oreg.

[73] Assignee: Melridge Inc., Aurora, Oreg.

[21] Appl. No.: 923,062

[22] Filed: Oct. 24, 1986

[51] Int. Cl.[4] ..... A01H 5/00

[52] U.S. Cl. ..... Plt./68

[58] Field of Search ..... Plt. 68

*Primary Examiner*—Robert E. Bagwill

*Attorney, Agent, or Firm*—Charles W. Rummler

[57] ABSTRACT

A new variety of hybrid lily plant bearing large clusters of flowers of excellent form and long persistence both on the plant and as cut flowers, the flowers being particularly distinguished by their light cream to white coloring and an unusual spotting pattern characterized by a small ring of tiny magenta spots; this combination being completely new in the upright Asiatic division of lilies suited to forcing and to mass commercial cultivation. This plant is an excellent garden plant, highly resistant to disease and showing high tolerance of virus. The bulbs may be precooled and forced for cut flower production and the clone is vigorous and is a good grower and propagator.

1 Drawing Sheet

BACKGROUND OF THE INVENTION

This new lily plant variety originated as a seedling selected from a group of seedlings planted at Sandy, Oreg., and resulting from my crossing the clonal cultivar 'Connecticut King' as the seed parent and as the pollen parent, an unnamed seedling clone selected from the cross of an upright white 'Hallmark' hybrid and the variety 'Sterling Star', with the object of producing lilies in cream and white color tones well suited to forcing for cut flower production out of season. My new plant was selected for propagation because of the large size and upright orientation of its flowers which had a soft cream to white color pattern accented by an unusual, dainty "ring" of spots and this propagation was done by me and under my direction at Sandy, Oreg., with such pleasing results that successive generations were produced by bulb scale propagation and by natural propagation from bulblets to demonstrate whether the novel characteristics of this new plant would hold true from generation to generation and would be firmly fixed.

The continued propagation of this new plant proved that the clone possessed to a high degree the desirable characteristics of hybrid vigor, great hardiness and disease resistance, as well as all of the desired characteristics of excellence of form, color and habit, as observed at Sandy, Oreg.

The new plant has shown to be well suited to forcing out of season when the bulbs are dug at the appropriate time and properly precooled; October-dug bulbs, properly precooled and potted in January, will flower under glass in western Oregon with no supplemental lighting and at moderate greenhouse temperatures in an average of 75 to 80 days.

DESCRIPTION OF THE DRAWING

My new variety of lily plant is illustrated by the accompanying photographic drawing, which shows a face view of a fully opened bloom in full color to illustrate the flower form and tepal arrangement and in particular, the distinctive lightly spotted, pale cream to white color pattern.

DESCRIPTION OF THE NEW VARIETY

The following is a detailed description of my new variety of Asiatic hybrid lily with nomenclature according to The International Lily Register of The Royal Horticultural Society, Second Edition, 1969, and with color designations according to The R.H.S. Colour Chart published in 1966.

THE PLANT

Origin: Seedling.

Parentage:

- *Seed parent.*—Lilium 'Connecticut King' (unpatented).
- *Pollen parent.*—An unnamed and unpatented white flower Lilium hybrid clone selected from the cross (W-14) of an upright white 'Hallmark' hybrid × 'Sterling Star'.

Classification:

- *Horticultural.*—Division I-A, Upright Asiatic Hybrid Lily, according to The Horticultural Classification of Lilies (The Royal Horticultural Society of London).
- *Commercial.*—Hybrid Lilium Clone.

Form: Single stem, erect and stately.

Height: About 75 to 100 cm. from bulbs of about 15 to 18 cm. in circumference, provided that the light levels are adequate. Low light levels may cause "stretching".

Growth: Vigorous and upright.

Foliage:

- *Quantity.*—Abundant.
- *Leaf size.*—About 8 to 15 cm. long and about 2 to 3 cm. wide.
- *Leaf shape*—Lanceolate with acuminate tip.
- *Texture.*—Leathery.
- *Aspect.*—Glossy and lightly pubescent along the margins.
- *Color.*—Deep green, somewhat lighter on the under side.

Bulbs:

- *Size.*—Various, ranging to 25 cm. in circumference in commercial use.
- *Color.*—White.

THE BUD

Form: Long ovoid with rounded base and obtuse apex.
Size: About 8 to 9 cm. long and about 5 cm. in circumference just prior to opening.
Opening rate: The bud opens slowly, taking about one hour in response to morning light.
Color: Palest cream to white just prior to opening and as the tepals unfurl.
Peduncle:
*Length.*—Averages about 4 to 6 cm., but may elongate if light levels are too low or if bulbs have been improperly stored prior to forcing.
*Color.*—Dark green with plum overlay.

THE FLOWER

Blooming habit: Annually, once and profusely in mid-season for Asiatic lilies.
Size: Large, averaging about 15 to 18 cm. in diameter.
Borne: As a single stem raceme producing 6 to 10 buds from a bulb of about 12 to 15 cm. in circumference.
Shape: Cup-shaped when first opening, then becoming flattened as the tepals recurve during the second day.
Petalage:
*Number.*—Six.
*Arrangement.*—Hexagonal with inner tepals closely imbricated over the outer tepals.
Shape: Ovate with rounded base and obtuse apex.
Appearance: Shiny.
Color: Very pale cream, 9D, at the base when the flowers first open, fading to pure white by the second day. There is an exceedingly narrow pencil stripe of deep magenta along the tepal margins extending about 2 to 3 cm. from the tepal base. The border of nectary furrows is lightly pubescent and white.
Tepal spotting: There is a small circle of small, deep magenta spots just above the nectaries about 2 cm. wide and forming a ring on the flower about 5 to 6 cm. in diameter.
*Color changes.*—The flower fades to pure white as the flower ages, if the light levels are adequate for cut flowers.
Appearance: The flower is shiny.
Pedicel:
*Length.*—About 6 to 10 cm., in average.
*Form.*—Sturdy and ascending up to about 45° and very rarely bearing secondary buds.
*Color.*—Dark green.
Persistence: The tepals stay on the stem about three weeks.
Fragrance: None.
Disease resistance: The flower and plant are resistant to disease; in particular, they are resistant to Botrytis blight and to Fusarium bulb rot.
Lasting quality: The flower is long lasting, both on the plant and as a cut flower.

THE REPRODUCTIVE ORGANS

Stamens:
*Number.*—Six.
*Arrangement.*—Typical of the genus Lilium.
*Anthers (dehisced) and pollen.*—Greyed orange, 167A.
Filaments:
*Length.*—About 5 cm.
*Color.*—Soft cream, 9D, to white.
Pistils:
*Number.*—One.
*Length.*—About 5 cm.
*Stigma.*—Color: Soft green with pale plum overlay.
Character of ovary: Typical of genus Lilium.

THE FRUIT

Fertility: The fruit is fertile.
Shape: Ovoid.
Color at maturity: Soft brown, sometimes overlaid with soft plum.

This variety of lily most closely resembles the variety 'Mt. Blanc' but it is distinguished by a soft cream yellow base color and delicate magenta pencil marks along the margins at the base of each tepal. This new variety is taller than 'Mt. Blanc', has a higher bud count, and is more reliable in its forcing performance. Also, it is more disease resistant and virus tolerant than the variety 'Mt. Blanc'.

I claim:

1. A new and distinctive variety of Asiatic hybrid lily, substantially as herein shown and described, particularly characterized by its excellence of flower form and its large, broadly tepalled flowers of soft cream to pure white coloration, enriched by a ring of small spots in the center of the flower and by a narrow pencil mark edging along the basal tepal margins; its vigorous growth and rapid natural propagation and its versatility both as a garden plant and as a cut flower producer from precooled bulbs forced under glass out of season.

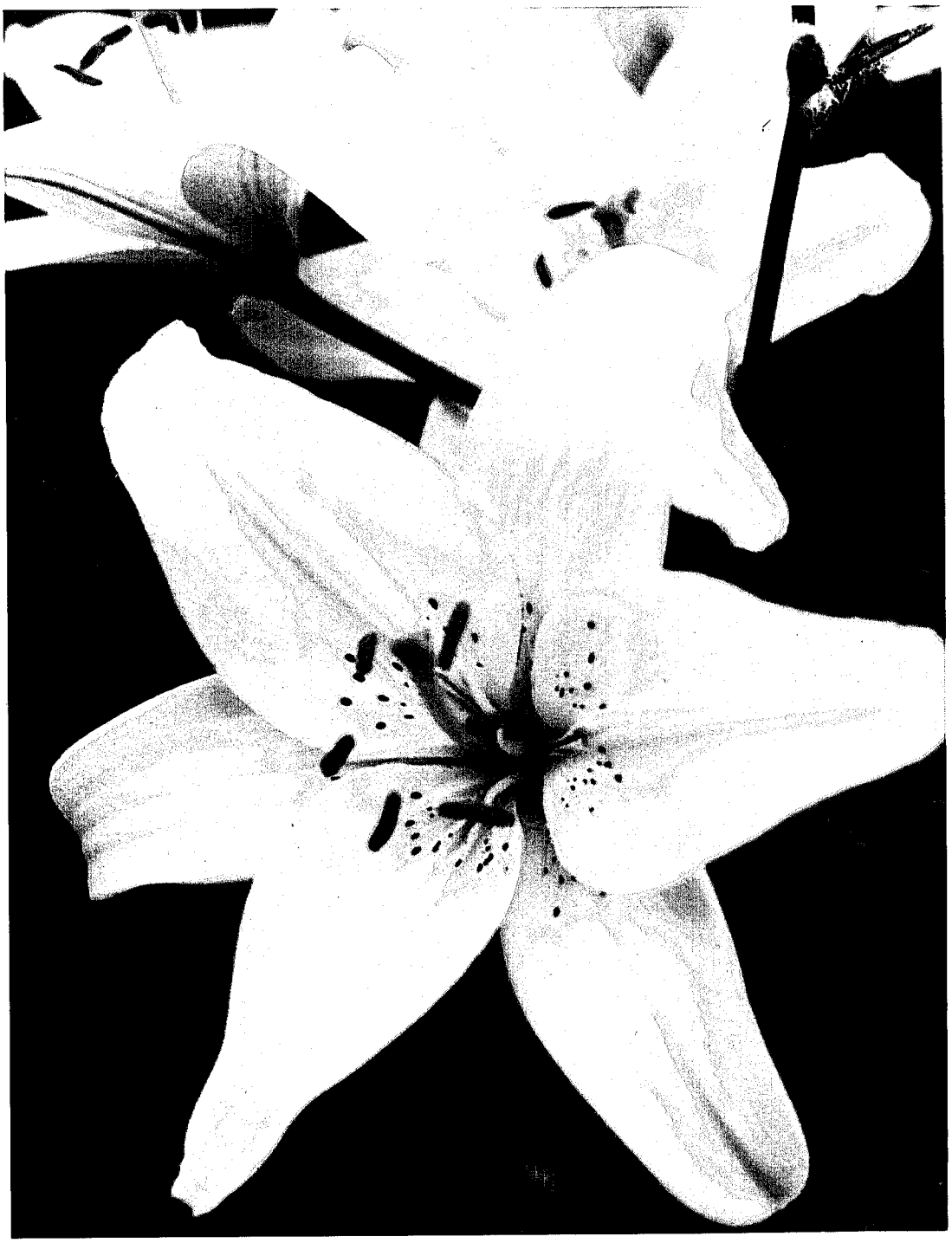

* * * * *